US007658932B2

(12) United States Patent
Karp

(10) Patent No.: US 7,658,932 B2
(45) Date of Patent: Feb. 9, 2010

(54) METHOD OF MAKING IMMUNOGENIC COMPOSITIONS COMPRISING UV-IRRADIATED, PSORALEN-INACTIVATED, DESIALATED HUMAN IMMUNODEFICIENCY VIRUS (HIV) PARTICLES DEVOID OF CD55 AND CD59 IN THE VIRAL MEMBRANE

(76) Inventor: Nelson M. Karp, 460 S. Independence Blvd., Virginia Beach, VA (US) 23462

( * ) Notice: Subject to any disclaimer, the term of this patent is extended or adjusted under 35 U.S.C. 154(b) by 0 days.

(21) Appl. No.: 12/315,777

(22) Filed: Dec. 5, 2008

(65) Prior Publication Data

US 2009/0098161 A1 Apr. 16, 2009

Related U.S. Application Data

(62) Division of application No. 10/971,445, filed on Oct. 22, 2004, now Pat. No. 7,556,814.

(51) Int. Cl.
*A61K 39/21* (2006.01)
*C12N 7/04* (2006.01)

(52) U.S. Cl. .................................... 424/208.1; 435/236

(58) Field of Classification Search ....................... None
See application file for complete search history.

(56) References Cited

U.S. PATENT DOCUMENTS

| | | | |
|---|---|---|---|
| 4,169,204 | A | 9/1979 | Hearst |
| 4,960,408 | A | 10/1990 | Klainer |
| 5,106,619 | A | 4/1992 | Wiesehahn |
| 6,107,543 | A | 8/2000 | Sims |
| 6,328,968 | B1 | 12/2001 | Van Lier et al. |
| 6,383,806 | B1 | 5/2002 | Rios |
| 6,503,753 | B1 | 1/2003 | Rios |
| 6,790,641 | B2 | 9/2004 | Schauber et al. |

FOREIGN PATENT DOCUMENTS

| | | |
|---|---|---|
| WO | WO 0220041 | 3/2002 |
| WO | WO 03024435 | 3/2003 |

OTHER PUBLICATIONS

Deichmann Marin et al: "Disinfection of Cell-Associated and Extracellular HIV-1 by PUVA Treatment" Journal of Virological Methods, vol. 68, No. 1, 1997, pp. 89-95, CONT.—XP002485905, ISSN: 0166-0934, pp. 94-95; figure 1.

Hart M L et al: "Glycosylation Inhibitors and Neuraminidase Enhance Human Immunodeficiency Virus Type Binding and Neutralization by Mannose-Binding Lextin" CONT.—Journal of General Virology, Society for General Microbiology, Spncers Wood, GB, vol. 84, 2, Feb. 1, 2003, pp. 353-360, XP009019190 ISSN: 0022-1317.

Pinter C et al: "Interference with Complement Regulatory Molecules as a Possible Therapeutic Strategy in HIV Infection" Expert Opinion on Investigational Drugs Feb. 2000 CONT.—vol. 9, No. 2 Feb. 1, 2000, pp. 199-205, XP002484637, pp. 200-201; figures 1, 2.

Saifuddin, M., et al., Human immunodeficiency virus type 1 incorporates both glycosyl phosphatidylinositol-anchored CD55 and CD59 and integral membrane CD46 at levels that cont.—protect from complement-mediated destruction J. Gen. Virol. 1997 vol. 78. pp. 1907-1911.

Aiken, C. et al., "Inside-out Regulation of HIV-1 Particle Fusion," Program and Abstracts of the 10th Conference on Retroviruses and Opportunistic Infections, Boston, MA USA Abstract 17 (Feb. 10-14, 2003).

Aroeti, Benjamin, et al., Mutational and Secondary Structural Analysis of the Basolateral Sorting Signal of the Polymeric Immunoglobulin Receptor, J. Cell Biology, vol. 123, No. 5, 1149-1160 (1993).

Ara, Yuki, et al., "Zymozan enhances the immune response to DNA vaccine for human immunodeficiency virus type-I through the activation of complement system" Immunology 103: 98-105 (2001), Japan.

Aslam, Mohammed, et al., "Folded Back Solution Structure of Monomeric Factor H of Human Complement by Synchrotron X-ray and Neutron Scattering, Analytical Ultracentrifugation and Constrained Molecular Modelling," Molecular Biology, vol. 309, pp. 1117-1138 (2001).

(Continued)

*Primary Examiner*—Jeffrey S. Parkin
(74) *Attorney, Agent, or Firm*—Williams Mullen

(57) ABSTRACT

A method of making an immunogenic composition using inactivated HIV. Inactivation of HIV is through psoralen and ultraviolet radiation. The composition is rendered more effective by the removal of structural features of HIV that interfere with immune response. In particular, sialic acid is removed to enhance immune recognition of the composition and to impair Complement Factor H binding. CD55 and CD59 are also removed to prevent the binding of Complement Factor H.

A method of making an immunogenic composition using inactivated HIV. Inactivation of HIV is through psoralen and ultraviolet radiation. The composition is rendered more effective by the removal of structural features of HIV that interfere with immune response. In particular, sialic acid is removed to enhance immune recognition of the composition and to impair Complement Factor H binding. CD55 and CD59 are also removed to prevent the binding of Complement Factor H.

20 Claims, 3 Drawing Sheets

OTHER PUBLICATIONS

Ault, Bettina, et al., "Human Factor H Deficiency," Biological Chemistry, vol. 272, #40, pp. 25168-25175 (1997), USA.
Blackmore, T. K., et al., "Identification of a Heparin Binding Domain in the Seventh Short Consensus Repeat of Complement Factor H," Immunology, vol. 157, Iss 12, pp. 5422-5427 (1996).
Braaten, D., et al., "Cyclophilin A regulates HIV-1 infectivity, as demonstrated by gene targeting of human T cells," the EMBO Journal, vol. 20, No. 6, pp. 1300-1309, 2001.
Brooks, Geo. F., Medical Microbiology Ch. 3 & 7 (23rd Ed. 2004).
Burger, R., et al., "Activation of the alternative pathway of complement: efficient fluid-phase amplification by blockade of the regulatory complement protein B1H through sulfated polyanions," European J. Immunology, vol. 11, pp. 291-295 (1981).
Doepper, Susi, et al, "Complement Receptors in HIV Infection," Current Molecular Medicine, vol. 2, Iss 8, pp. 703-711 (2002).
Burger, R., et al., "Dextran Sulphate: a Synthetic Activator of C3 via the Alternative Pathway," Immunology, vol. 29. pp. 549-554 (1975).
Burger, R., et al., "Insoluble polyanions as activators of both pathways of complement," Immunology 33:827-837 (1977).
Chan, D. C., et al., "Core Structure of gp41 from the HIV Envelope Glycoprotein" Cell, vol. 89, Issue 2, pp. 263-273 (Apr. 18, 1997).
Chen, Chien-Hung, et al., "Enhancement of DNA Vaccine Potency by Linkage of Antigen Gene to an HSP70 Gene," Cancer Research 60:1035-1042 (Feb. 15, 2000).
Cheng, Wen-Fang, et al., "Tumor-specific immunity and antiangiogenesis generated by a DNA vaccine encoding calreticulin linked to a tumor antigen," Journal of Clinical Investigation, vol. 108, No. 5, 669-678 (Sep. 2001).
Hung, Chien-Fu, et al., "Enhancing Major Histocompatibility Complex Class I Antigen Presentation by Targeting Antigen to Centrosomes," Cancer Research 63: 2393-2398 (May 15, 2003).
Cohen, P.T., The AIDS Knowledge Base, 15-18,21 (3rd ed. 1999).
Cummings, Melissa, et al., New Research Uncovers Potential for More Effective Anti-HIV Therapies: Essential Role of Cyclophilin, Novel Non-Mutable Drug Target Discovered, PR NewsWire 1996.
Dierich, M. P., et al., "HIV and human complement: mechanisms of interaction and biological implication," Immunology Today, vol. 14, lss 9, pp. 435-440 (1993).
Discipio, R. G., "Ultrastructures and interactions of complement factors H and 1," .J. Immunology, vol. 149, Iss 8, pp. 2592-2599 (1992).
Fearon, D.T., et al., "Activation of the alternative complement pathway due to resistance of zymosan-bound amplification convertase to endogenous regulatory mechanisms," Proc. Natl. Acad. Sci, vol. 74, No. 4, pp. 1683-1687 (Apr. 1977).
Feifel, Elisabeth, et al., "Polymorphism and deficiency of human factor H-related proteins p39 and p37," Immunogenetics, vol. 36, pp. 104-109 (1992).
Fishelson, Z., et al., "C3 Convertase of Human Complement: Enhanced Formation and Stability of the Enzyme Generated with Nickel instead of Magnesium," J. of Immun., vol. 129, No. 6, pp. 2603-2607 (Dec. 1982).
Forrest, Bruce D., et al., "Effect of Parenteral Immunization on the Intestinal Immune Response to Salmonella typhy Ty2la," Infection and Immunity, vol. 60, No. 2, pp. 465-471 (Feb. 1992).
Franke, E. K., et al., "Chaperoning a pathogen," Nature, 372 (6504): 319-20 (Nov. 24, 1994).
Franke, E. K., et al., "Specific Incorporation of Cyclophilin A Into HIV-1 Virions," Nature, 372(6504): 359 (Nov. 24, 1994).
Friese, M. A., "FHL-1/reconectin and factor H: two human complement regulators which are encoded by the same gene are differently expressed and regulated," Molecular Immunology, vol. 36, pp. 809-818(1999).
Furie, Bruce, "Oral Anticoagulant Therapy," Hematology Basic Principles & Practice, Ch. 121, pp. 2040-2046 (3rd ed. 2000).
Gardner, William D., "Identification of a major human serum DNA-binding protein as B1H of the alternative pathway of complement activation," Biochemical and Biophysical Research Communications, vol. 94, pp. 61-67 (1980) .
Gasque, P., "Expression of complement components of the alternative pathway by glioma cell lines," Immunology, 149:1381-87(1992).
Giannakis, Eleni, et al., "Multiple ligand binding sites on domain seven of human complement factor H," Int'l. Immunopharmacology, vol. 1, Issue 3, pp. 433-443 (2001).
Goudsmit, J., Immunodominant B-Cell epitopes of the HIV-1 envelope recognized by infected and immunized hosts, AIDS, vol. 2 (Suppl 1): S41-S45 (1988).
Gowda, D. C., et al., "Immunoreactivity and Function of Oligosaccharides in Cobra Venom Factor," J. of Immun., vol. 152, Issue 6, pp. 2977-2986 (Dec. 1993).
Harrison, Stephen, Howard Hughes Medical Institute, Remarks for Institute News titled "HIV's Deep Pocket May Reveal Vulnerability; Seeing the Structure of the Viral Protein gp41 suggested the experimental design" (Sep. 28, 1999); Internet: www.hhmi.org/news/gp41.html.
Haurum, John, "Complement activation upon binding of mannan-binding protein to HIV envelope glycoproteins," AIDS, vol. 7 (10), pp. 1307-1313 (1993).
Hellwage, J., "Functional Properties of complement factor H-related proteins FHR-3 and FHR-4: binding to the C3d region of C3b and differential regulation by Heparin," FEBS Lett., 462(3): 345-352 (Dec. 3, 1999).
Hoffman, Ronald, Hemotology Basic Principles and Practice, Ch. 36, pp. 640-651; Ch. 37, pp. 651-667; Ch. 39, pp. 686-701 (3rd ed. 2000).
Hogan, Christine M., et al., "Host Determinants in HIV Infection and Disease," Ann. Intern. Med. 13(10): 978-996 (2001).
Hughson, F.M., "Enveloped viruses: A common mode of membrane fusion?" Current Biology 7(9): R565-R569 (1997).
Hughes, Huw, "Bacterial Vectors for Vaccine Delivery," Designer Vaccines: Principles for Successful Prophylaxis, Ch. 2, 8, pp. 151-178(1998).
Joiner, K. A., "Complement Evasion by Bacteria and Parasites," Ann. Rev. Microbiol, vol. 42, pp. 201-230 (1988).
Johnston, Margaret, et al., "Progress in HIV vaccine development", Current Opinion in Pharmacology, 1:504-510 (2001).
Jokiranta, T., "Analysis of the recognition mechanism of the alternative pathway of complement by monoclonal anti-factor H antibodies: evidence for multiple interactions between H and surface bound C3b," FEBS Lett., 393: 297-302 (Sep. 16, 1996).
Jokiranta, T., "Each of the Three Binding Sites on Complement Factor H Interacts with a Distinct Site on C3b," J of Biological Chemistry, vol. 275, #36, 27657-27662 (Sep. 8, 2000).
Kaplan, G., et al., "Construction and Characterization of Poliovirus Subgenomic Replicons," J. Virol. 62(5):1687-96 (May 1988).
Kaufmann, Stefan H. E., Concepts in Vaccine Development, Ch. 2, 3.7 (1996).
Keren, David F., et al., "Combined Parenteral and Oral Immunization Results in an Enhanced Mucosal Immunoglobulin A Response to *Shigella flexneri*," Infect. lmmun. 56: 910-915 (1988).
Kirkitadze, Marina, et al., "Structure and flexibility of the multiple domain proteins that regulate complement activation," Immun. Rev., vol. 180, pp. 146-161 (2001).
Kitamura, N. et al., "Primary structure, gene organization and polypeptide expression of poliovirus RNA," Nature 291: 547-553 (1981).
Kiyono, Hiroshi, et al., Mucosal Vaccines, Prospects for Induction of Mucosal Immunity by DNA Vaccines, Ch. 8, pp. 119-127(1996).
Kock, Michael A., et al., "Structure and function of recombinant Cobra Venom factor," J. of Biol. Chemistry, vol. 279 pp. 30836-30843 (2004).
Lachmann, P. J., "The influence of C3b Inactivator (KAF) Concentration on the Ability of Serum to Support Complement Activation," Clin. exp. Immonol., vol. 21, pp. 109-114 (1975).
Lee, Young-Min, et al., "A Bipartite Membrane-Binding Signal in the Human Immunodeficiency Virus Type 1 Matrix Protein is Required for the Proteolytic Processing of Gag Precursors in a Cell Type-Dependent Manner," J. of Virology, pp. 9061-9068 (Nov. 1998).
Legendre, C., et al., "Mechanisms of opsonized HIV entry in normal B lymphoytes," FEBS Lett. 381:227-232 (1996).
Levinson, Warren, et al., Medical Microbiology & Immunology, Chanpter 58, pp. 363-381, 401 (7th ed. 2002).
Levy, J. A., "Pathogenesis of Human Immunodeficiency Virus Infection," Microbiol. Rev. 57(1): 183-289 (1993).

Lewis, P.J., et al., “Altering the Cellular Location of an Antigen Expressed by a DNA-Based Vaccine Modulates the Immune Response” Journal of Virology, 73 (12): 10214-10223 (Dec 1999).
Liang J.F, et al., “A Less Toxic Heparin Antagonist-Low Molecular Weight Protamine,” Biochemistry, vol. 68 (1): 116-120(2003).
Maillet, Francoise, et al., “Heparin Prevents Formation of the Human C3 Amplification Convertase by Inhibiting the Binding Site for B on C3b,” Molecular Immun., vol. 20 (12): 1401-1404 (1983).
Maillet, Francoise, et al., “Structure-function Relationships in the Inhibitory Effect of Heparin on Complement Activation: Independency of the Anti-coagulant and Anti-complementary sites on the Heparin Molecule,” Mol. Immun., vol. 25 (9): 917-923 (1988).
McRae, Jennifer, et al., “Human Factor H-related Protein 5 (FHR-5),” Biological Chemistry, vol. 276 (9): 6747-6754 (2001).
McMichael, Andrew J., et al., “Cellular Immune responses to HIV, Nature,” 410:980-987 (Apr. 19, 2001).
Meri, Seppo, et al., “Discrimination between activators and nonactivators of the alternative pathway of complement: Regulation via a sialic acid/polyanion binding site on factor H,” Proc. Natl. Acad. Sci., USA, vol. 87, pp. 3982-3986 (May 1990).
Michalek, Michael T., et al., “Inhibition of the Alternative Pathway of Human Complement by Structural Analogues of Sialic Acid,” J. Immunology, vol. 140, pp. 1588-1594 (1988).
Morrow, W.J., et al., “Circulating Immune Complexes in Patients with Acquired Immune Deficiency Syndrome Contain the AIDS-Associated Retrovirus,” Clin. Immunol. and Immunopathol., 40:515-24 (1986).
Nicholl, Desmond, An Introduction to Genetic Engineering, Ch. 3, 5 (2nd Ed 2002).
Nilsson, U. R., et al., J. Exp. Med. 122: 277-298 (1965).
Ono, Akira, et al., “Binding of Human Immunodeficiency Virus Type 1 Gag to Membrane: Role of the Matrix Amino Terminus, J. of Virology,” vol. 73, No. 5, pp. 4136-4144 (May 1999).
Pangburn, M. K., “Analysis of Recognition in the Alternative Pathway of Complement: Effect of Polysaccharide Size,” J. of Immunol., vol. 142 (8): 2766-2770 (Apr. 1989).
Pangburn, M. K., “Molecular Mechanisms of Target Recognition in an Innate Immune System: Interactions Among Factor H, C3b, and Target in the Alternative Pathway of Human Complement,” .J. of Immunol., vol. 164, pp. 4742-4751 (2000).
Pantaleo, G., et al., “Studies in Subjects With Long-Term Nonprogressive Human Immunodeficiency Virus Infection,” N. Engl. J. Med., vol. 332, No. 4, 332:209-16 (1995).
Parham, Peter, The Immune System, Ch. 7, 12 (2nd Ed 2004).
Pinter, Claudia, et al.,“HIV Glycoprotein 41 and Complement Factor H Interact with Each Other and Share Functional as Well as Antigenic Homology,” Aids Research in Human Retroviruses, vol. 11(8): 971-80 (Nov 8, 1995).
Pinter, Claudia, et al., Direct Interaction of Complement factor H with the Cl Domain of HIV Type 1 Glycoprotein AIDS Research and Human Retroviruses, vol. 11 (5): 577-588 (1995).
Porter, Donna C., et al., Encapsidation of Poliovirus Replicons Encoding the Complete Human Immunodeficiency Virus Type 1 gag Gene by Using a Complementation System Which Provides the PI Capsid Protein in trans, Journal of Virology, vol. 69 (3): 1548-1555 (Mar. 1995).
Presanis J.S., et al., “Biochemistry and genetics of mannan-binding lectin (MBL),” Biochemical Society Transactions, vol. 31, Part 4, pp. 748-752 (2003).
Procaccia, S., et al., “Rheumatoid factors and circulating immune complexes in HIV-infected individuals, ”AIDS, vol. 5(12): 1441 (1991).
Racaniello, V. R., et al., “Molecular cloning of poliovirus cDNA and determination of the complete nucleotide sequence of the viral genome,” Proceedings of the National Academy of Sciences, USA, 78 (8): 4887-4891 (Aug. 1981).
Reisenger, E. C., et al., “Complement-mediated enhancement of HIV-1 infection of the monoblastoid cell line U937,” AIDS, vol. 4, pp. 961-965 (1990).
Ren, R., et al., “Human Poliovirus Receptor Gene Expression and Poliovirus Tissue Tropism in Transgenic Mice,” J. of Virol. 66 (1): 296-304 (1992).
Resh, Marilyn D., “A myristoyl switch regulates membrane binding of HIV-1 Gag,” Proc. Natl. Acad. Sci., vol. 101 (2) 417-418 (Jan 13, 2004).
Ripoche, Jean, et al., “The complete amino acid sequence of human complement factor H,” Biochem. J., vol. 249, pp. 593-602 (1988).
Robinson Jr., W. E., et al., “Antibody-Dependent Enhancement of Human Immunodeficiency Virus Type 1 Infection”, The Lancet, pp. 790-794 (Apr. 1988).
Sahu, Arvind, et al., “Specificity of the thioester-containing reactive site of human C3 and its significance to complement activation,” Biochem. J., vol. 302, pp. 429-436 (1994).
Sande, Merle A., et al., the Medical Management of AIDS (6th ed. 1999).
Saphire Andrew C.S., et.al., “Host cyclophilin a mediates HIV-1 attachment to target cells via heparans,” The EMBO Journal, vol. 18, #23, pp. 6771-6785 (1999).
Sherry, Barbara, et al., “Role of cyclophilin A in the uptake of HIV-1 by macrophages and T lymphocytes,” Proc. Natl. Acad. Sci., vol. 95, pp. 1758-1763 (1998).
Skerka, C., et al., “Mapping of the Complement Regulatory Domains in the Human Factor H-like Protein 1 and in Factor H,” J. of Immun., 155(12): 5663-5670 (Dec. 1995).
Smith, Colleen, Basic Medical Biochemistry: A Clinical Approach, Ch. 17 (2d. ed. 1996).
Spear G. T., et al., “Human immunodeficiency virus (HIV)-infected cells and free virus directly activate the classical complement pathway in rabbit, mouse and guinea-pig sera; activation results in virus neutralization by virolysis,” J. Of Immunology, vol. 73, pp. 377-382 (1991).
Speth, C., et al., “Complement receptors in HIV infection,” Immunological Reviews, vol. 159, pp. 49-67 (1997).
Speth, C., et al., “The complement system: Pathophysiology and clinical relevance,” The Middle European J. of Medicine, 111/10: 378-391 (1999).
Stahl, Stefan, et al., “Strategies for Gene Fusions, ”Methods in Molecular Biology, 62: 37-54 (1997).
Stoiber, Heribert, et al., “The envelope glycoprotein of HIV-1 gp120 and human complement protein Cl q bind to the same peptides derived from three different regions of gp41, the transmembrane glycoprotein of HIV-1, and share antigenic homology,” European J. of Immun., vol. 24, pp. 294-300 (1994).
Stoiber, Heribert, et al., “Human Complement Proteins C3b, C4b, Factor H and Properdin React with Specific Sites in gp120 and gp4I, the Envelope Proteins of HIV-1,” Immunobiology, vol. 193, pp. 98-113(1995).
Stoiber, Heribert, et al., “Efficient Destruction of Human Immunodeficiency Virus in Human Serum by Inhibiting the Protective Action of Complement Factor H and Decay Accelerating Factor (DAF, CD55),” J. Exp. Med., vol. 183, pp. 307-310 (Jan. 1996).
Stoiber, Heribert, et al., “Role of Complement in HIV Infection,” Annu. Rev. Immunol, 15:649-674 (1997).
Stoiber, Heribert, “Role of Complement in the control of HIV dynamics and pathogenis,” Vaccine, 21: S2/77-S2/82 (2003).
Sun, Jiangfeng, et al., “Syncytium Formation and HIV-1 Replication Are Both Accentuated by Purified Influenza and Virus-associated Neuraminidase,” J. of Biol. Chemistry, 277 (12): 9825-9833 (2002).
Tang, Chun, et al., “Entropic switch regulates myristate exposure in the HIV-1 matrix protein,” Proc. Nat’l Acad. Of Sci., 101 (2): 517-522 (Jan. 2004).
Thali, M., et al., “Functional association of cyclophilin A with HIV-1 virions,” Nature, 372 (6504): 363-5 (1994).
Thieblemont, N., et al., Triggering of Complement Receptors CRI (CD35) and CR3 (CD11 b/CD18) Induces Nuclear Translocation of NF-KB (p50/p65) in Human Monocytes and Enhances Viral Replication in HIV-Infected Monocytic Cells, J. of Immunology, vol. 155, p. 4861-4867 (1995).
U.S. Environmental Protection Agency, Health Assessment Document for Nickel. EPA/600/8-83/012F. National Center for Environmental Assessment, Office of Research and Development, Washington, DC 1986.
Vajdos, Felix, et al., Crystal structure of cyclophilin a complexed with a binding site peptide from the HIV-1 capsid p. Protein Science 6(11): 2297-2307 (1997)

Vogel, Carl W., "Antibody Conjugates without Inherent Toxicity: The Targeting of Cobra Venom Factor and Other Biological Response Modifiers," Immunoconjugates, Ch. 9, pp. 170-188(1987).

Wagner, Edward K., Basic Virology, pp. 105-108, 368 (1999).

Walker, Christopher, et al., "Cationic lipids direct a viral glycoprotein into the Class 1 major histocompatibility complex antigen-presentation pathway," Proc. Natl. Acad. Sci., 89: 7915-7918 (Sep. 1992).

Weiler, John M., et al., "Modulation of the formation of the amplification convertase of complement, C3b,Bb, by native and commercial Heparin," J. Exp. Med., vol. 147, pp. 409-421 (1978).

Weissenhorn, W., et al., "Atomic structure of the ectodomain from HIV-1 gp41," Nature, vol. 387, pp. 426-430 (May 1997).

Paul, William E., Fundamental Immunology, pp. 967-995 (4th ed. 1999).

Winkelstein, J. A., et al., "Activation of the Alternative Complement Pathway by Pneumococcal Cell Wall Tcichoic Acid," J. of Immun., vol. 120, pp. 174-178 (1978).

Zipfel, P.F., et al., "Complement factor H and related proteins: an expanding family of complement-regulatory proteins?" Immunology Today, 15(3): 121-126 (1994).

Azadegan, A.A., 1984, "Cobra Venom Factor Abrogates Passive Humoral Resistance to Syphilltic Infection in Hamsters", Infect. Immun. 44(3): 740-742.

Cycloaddition

Psoralen

Thymine (10b)

Cycloadduct

METHOD OF MAKING IMMUNOGENIC COMPOSITIONS COMPRISING UV-IRRADIATED, PSORALEN-INACTIVATED, DESIALATED HUMAN IMMUNODEFICIENCY VIRUS (HIV) PARTICLES DEVOID OF CD55 AND CD59 IN THE VIRAL MEMBRANE

CROSS REFERENCE TO RELATED APPLICATIONS

The present Divisional Application claims priority from co-pending U.S. patent application Ser. No. 10/971,445 filed Oct. 22, 2004 which claims priority to U.S. Provisional application Ser. No. 60/513,827 filed Oct. 23, 2003; which are hereby incorporated by reference.

BACKGROUND OF THE INVENTION

1. Field of the Invention

This invention relates to the fields of virology and immunology. Particularly, but not exclusively, it relates to a method of inducing an immune response to HIV using a psoralen inactivated composition of HIV and a substance for achieving the same.

2. Description of the Related Art

Human Immunodeficiency Virus

Human Immunodeficiency Virus (HIV) is a retrovirus within the slow or Lentivirus group, and is the cause of Acquired Immunodeficiency Syndrome (AIDS). Some retroviruses that attack the immune system, such as HIV-1, are variable and mutate readily, creating many strains of varying genetic composition that hamper efforts to develop effective treatment. These strains, which may be categorized into groups or subtypes, have individual biological characteristics. Sequences within a subtype may have genetic clustering or similarities that differences among mutations even within a subtype. Further, the tendency of retroviruses to recombine with related retroviruses complicate the viral genotype.

HIV uses its RNA as a template for making complementary viral DNA in target cells through reverse transcription, viral DNA can then integrate into the DNA of an infected host. HIV infects cells having surface CD4, such as lymphocytes, monocytes, dendritic cells and macrophages, and destroys CD4 positive helper T lymphocytes. This process relies in part on two glycoproteins of HIV. These glycoproteins are gp120 (an Env glycoprotein, the exterior receptor-binding component) and a non-covalently interacting partner, gp41 (the Env transmembrane glycoprotein.) Gp120 and gp41 are associated in a trimeric unit, where three molecules of gp 120 are exposed on the virion surface and are associated with three molecules of gp41 in the viral lipid membrane. Gp 120 binds to a CD4 receptor on the surface of helper T cells. This binding is generally considered to be high affinity, and can be further enhanced by high sialic acid content on the surface of the virus; sialic acid reduces the threshold binding energy needed to overcome repulsive electrostatic forces. The virus then begins to fuse with the T cell, producing structural or conformational changes and exposing other receptors. Upon fusion, the gp120 fragment is shed, exposing the gp41 ectodomain in a process that also varies conformationally. Gp41 is then available to project peptide fusion domains for binding to the target cell. This leads to HIV entering and infecting the target cell.

The envelope of HIV begins formation from the plasma membrane of the host cell when the virus buds through the cell membrane. Thus, the envelope includes the lipid and protein constituents of the host cell. (Frank, Ines, Heribert Stoiber, et al., Vol. 10, pp. 1611-20 (1996)) (Stoiber, Heribert, et al., Vol. 15, pp. 649-74 (1997)) Some enveloped viruses use spike proteins to mimic the host molecules in order to bind to target cell receptors and to enter other target cells. However, these spikes can also be antigenic surfaces for immune system recognition. Yet HIV offers protection. In addition to the variability of conformational changes, gp120 provides other surface features that disguise it from immune detection and attack, such as a coating of glycoproteins, covalently bound sialic acid residues, or steric occlusion. (Haurum, John, Treffen Thiel, et al., Vol. 7(10), pp. 1307-13 (October 1993)) (Sande, Merle, et al., The Medical Management of Aids, (6th ed. 1999)) (Cohen, P. T., The AIDS Knowledge Base, (3rd ed. February 1999))

The core of the HIV virion functions as a command center. Inside an HIV virion is a capsid composed of the viral protein, p24 (CA). The capsid holds two single strands of RNA, each strand of which provides a copy of HIV's nine genes, which encode 15 proteins. Of the nine genes, three (gag, pol and env) are considered essential. Six additional genes are also found within the 9-kilobase pair RNA genome (vif, vpu, vpr, tat, rev and nef) More specifically, the env gene holds the information or code for creation of gp160, which breaks down into gp120 and gp41. Likewise the gag gene encodes the matrix (p17 or MA), capsid (p24 or CA), nucleocapsid (p9 or NC) and p6. The pol gene provides the genetic information for the virus to produce the reverse transcriptase enzyme as well as the integrase enzyme and RNAse H enzyme. The other six genes are regulatory, and control the mechanisms of infection and replication (vif, vpu, vpr, tat, rev and nef). Among other things, the nef gene holds information for efficient replication, while vpu holds information regulating the release of new viral particles from the infected host cell. Ultimately, in order for HIV to infect a target cell, it must inject the HIV genetic material into the target cells cytoplasm.

As noted above, the nef gene is believed to aid efficient replication of HIV. The creation of a new virus particle occurs at the host cell's membrane. Nef appears to affect an infected cell's environment in a way that optimizes replication. Viral proteins collect near the host cells membrane, bud out within the membrane, and break away. These proteins are the three structural proteins (gp160, gp120, gp41) plus two other internal precursor polyproteins (Gag and the Gag-Pol). The Gag-Pol protein brings two strands of the positive RNA into the bud, while protease cuts itself free. After the virus has budded, protease cuts itself free and cuts up the rest of the proteins in Gag or Gag-Pol, releasing the various structural proteins and reverse transcriptase. The viral proteins are not functional until they are separated by the protease. Thus, protease is responsible for cleavage of Gag-Pol and the smaller Gag polyprotein into structural proteins. Released proteins p24, p7 and p6 form a new capsid, while at the base of the lipid membrane is p24. In this process, gp160 breaks down into gp120 and gp41 by a host enzyme.

Most HIV vaccines use portions of the envelopes of these glycoproteins (gp160, gp120, and gp41) in an attempt to induce production of neutralizing antibodies against the envelope spikes of the virus. (Johnston, et al., 2001) Some have been successful in producing high titers of neutralizing antibodies. The thought behind this approach is that the antibodies that bind to these glycoproteins would neutralize the virus and prevent infection. A functioning immune system could then activate the complement system, which would cascade to lysis and destroy the virus. The complement system is a series of circulating proteins that "complements" the role of antibodies. The components of the complement system are activated in sequence or turn, which is the complement cascade. The conclusion of complement is a protein complex, the Membrane Attack Complex (MAC) that seeks to attach to an invading organism's surface and to destroy it by puncturing its cell membrane.

However, HIV provides an additional protection against humoral immune response. HIV will activate human complement systems even in the absence of specific antibodies. This activation would be harmful to the virus if complement were left unimpeded to reach MAC, triggering virolysis. However, HIV avoids virolysis by incorporating into its structure various molecules (e.g., CD55, CD59) that regulate complement. HIV includes these cell membrane molecules in the virus membrane upon budding from infected cells, or by attachment to gp41 and gp120. Complement Factor H may be incorporated into the structures of both gp41 and gp120. Factor H inhibits the activity of C3b, a molecule that is central within complement cascade. This interaction with complement components enables HIV to take advantage of complement activation to enhance infectivity, follicular localization, and target cell range.

Vaccine Therapy and Related Art

Immunotherapy involves the use or stimulation of the immune system with respect to a condition or sensitivity. Vaccines are a form of immunotherapy. In 1955, Dr. Salk introduced the poliovirus vaccine; this vaccine used the chemical formaldehyde (formalin) to kill the virus or render it non-infective or inactive, so that it could be administered to patients. In 1961 Dr. Sabin introduced a live attenuated relatively avirulent poliovirus vaccine. The Sabin vaccine was basically composed of viral mutants capable of eliciting an immune response but not capable of significant active replication or virulence, and therefore were considered relatively safe for human use.

There have been effective vaccines against retroviruses in animals. One vaccine is available for feline immunodeficiency retrovirus (or FIV) (i.e., Fel-O-Vax); a second example is a vaccine against Equine Infectious Anemia Virus (or EIAV), (i.e., EIAV(UK)deltaS2) an important retroviral infection of horses. These vaccines argue powerfully that vaccines can work against retroviruses, although neither disease is an ideal model for HIV in humans. (Beyer, 2003)

However, a vaccine for HIV has proven elusive. The vast majority of vaccines under consideration, research, or trials are comprised of either "live" attenuated viral particles or whole inactivated viral particles. The use and research of recombinant technology, adenoviral vectors, DNA-based vaccines or a combination thereof has tested the boundaries of immunology, offering some hopes for addressing HIV. Such immunogenic compositions could be used for the following purposes:

To enhance the immune system of a person who has already been infected with the disease systemically.

To prevent a person from contracting the disease after exposure.

To prevent a person from contracting the disease prior to exposure. This is the most common use for a vaccine today.

To prevent a patient from contracting a different strain of HIV disease, particularly non-compliant or immunosuppressed patients.

To prevent vertical transmission from mother to fetus or from mother to newborn.

To attenuate HIV disease in an HIV negative patient who contracts the disease at a later date To research potential compositions and methods for any of the purposes above Unfortunately, medicine lacks a definition for HIV immunity. (Gonsalves, Gregg, Basic Science (2000)) (Cohen, 1999) This is a fundamental problem with an important consequence: there is no known correlate of protection against HIV. However, there are well-characterized correlates for disease progression, such as viral loads and CD4 counts. Furthermore, there is no evidence that any of the current candidate vaccines can elicit responses in HIV-positive patients that would improve these parameters (viral loads and CD4 counts) for an extended period. (Beyrer, Chris, "The HIV/AIDS Vaccine Research: An Update." The Hopkins Report (January 2003)) Additionally, while there have been advances in some animal models, there is no validated animal model system for testing vaccine candidates, an obvious limitation when working with a high fatality pathogen such as HIV. (Beyrer, 2003) Current life expectancy after contracting HIV disease is approximately 10 to 15 years. Even a vaccine that failed to prevent transmission but extended life expectancy of a patient after contracting the disease would constitute an improvement.

Inactivated viruses may be useful for research and medicine. In fact, most of the successful early vaccines relied on inactivated virus. Inactivation produces a virus that is not infective, yet still induces an immune response based on its residual characteristics. An inactivated virus is typically generated from stocks of a virulent strain grown in cultured cells or animals. A potentially virulent virus is then made non-infectious or inactivated by chemical treatment. Viruses are by definition non-viable entities; they do not consume oxygen and food, nor do they produce waste; they replicate via their host, as described above for HIV. Viruses have no inherent metabolic activity and do not produce adenosine triphosphate (ATP). However, a live virus vaccine is capable of reproduction, while a killed virus vaccine is not. In general, live vaccines are more efficacious but also more dangerous than killed vaccines.

When a virus is inactivated, an immunogenic composition based on inactivated virus must retain its antigenicity in order to be useful. The inactivation process should preserve the three-dimensional structure of the virus while at the same time eliminating its virulence. Many methods are available to inactivate or kill a virus, but most destroy or change the three-dimensional structure of the virion, harming its antigenic characteristics. Originally, formaldehyde (formalin) treatment was used; for example, the Salk poliovirus vaccine was a formalin-inactivated preparation of three virus serotypes. Despite its wide use in early vaccines, formalin is difficult to remove and therefore poses the danger of residual toxicity. More recently, β-propriolactone has become a commonly used chemical to inactive a virus because residual amounts of the reagent can be readily hydrolyzed into non-toxic products. U.S. Pat. No. 4,169,204 to J. Hearst, et al., suggested the use of psoralens with irradiation to inactivate viruses for vaccine preparation. Psoralens are attractive because of their ability to inactivate virus without damaging the structure and without harmful residue. (Hanson, C. V., Bloodcells, Vol. 18(1), pp. 7-25 (1992)) Psoralens occur naturally in plants, including limes and celery, which use them to attack insects and fungi.

As noted above, the general notion of using psoralen to inactivate viruses is known. For example, U.S. Pat. No. 5,106,619 disclosed psoralen inactivation of a live virus in order to prepare vaccines. That invention involved treatment or inactivation of virions using furocoumarins, including 4'-aminomethyl-4,5', 8-trimethylpsoralen hydrochloride (AMT), and ultraviolet light in a limited oxygen environment. The inactivation is directed to double and single stranded DNA viruses, double and single stranded RNA viruses, and enveloped and non-enveloped viruses. This disclosure was general, and did not specifically contemplate HIV.

Some inventors have contemplated the use of psoralen in an HIV vaccine or composition. U.S. Pat. No. 6,107,543 disclosed a whole particle HIV immunogen that is inactivated preferably by gamma radiation; also disclosed, however, are a variety of alternative inactivation methods including psoralen, formalin, β-propriolactone, etc. The whole particle is treated for removal of the outer envelope proteins gp 120 or gp160, while retaining the remainder of the structure. An alternative embodiment is a reduced immunogen comprising the remaining purified gene products, such as those encoded by the gag genes, the pol genes, the trans-membrane protein gp41, or the remaining genes of the HIV genome.

U.S. Pat. Nos. 6,383,806 and 6,503,753 disclosed a composition and method for development of an HIV vaccine based on psoralen photoinactivation of Reverse Transcriptase (RT). In other words, the objective of this invention is to promote an immune response based on the inactivation of a single inactivated enzyme within HIV. Preservation of the remainder of the particle is deemed to enhance immune response to the composition.

Although psoralen has been contemplated by inventors for use in an HIV immunogen or vaccine, none have looked to certain structural preservation issues inherent with psoralen inactivation of HIV. For example, HIV is highly mutagenic, changing structures frequently in the process of reverse transcription. Mutation may provide a means for an HIV strain to escape immune response caused by a vaccine. (Cohen, 1999) In addition, the preservation of HIV structure may result in the preservation of HIV components that disadvantage immune response.

Past efforts have not focused on the problems of mutation. HIV is a highly mutagenic retrovirus which, through reverse transcriptase converts its RNA into DNA. HIV reverse transcriptase is error prone, leading to mutation. Further, rapid replication exacerbates mutation. The high level of genomic diversity in HIV complicates diagnosis, treatment, and public health monitoring of disease progression. In particular, this diversity is manifested in biological peculiarities characterizing as infectivity, transmissibility, and immunogenicity. The divergence in viral genotypes of HIV has contributed to polymorphism, transmission efficiency, and the historical epidemic development of HIV. The variety of subtypes and sub-subtypes with each having a peculiar three dimensional structure can render a subtype vaccine ineffective for a patient having a different subtype. The high rate of mutation of HIV is certain to complicate selection of the appropriate immunogen.

The preservation of HIV structural components may present performance issues. As with U.S. Pat. No. 5,106,619, both U.S. Pat. Nos. 6,383,806 and 6,503,753 preserve whole particles. The later inventions are directed to inactivating only the RT. The preservation of the antigenic structure is intended to take advantage of a wider range of immunogens. This preservation of the correct antigenic conformation is considered important for access to the cytoplasm via micropinocytosis or mannose-receptor mediated uptake at dendritic cells. U.S. Pat. No. 6,107,543 includes psoralen inactivation within its disclosed method, but conversely required the removal of envelope glycoproteins gp 120 and gp 160 (but not gp41) because antibodies to those glycoproteins might facilitate virus absorption to cells. In fact, it is known that HIV can bind to and use C3b as ligands to permit infectious immune complexes to bind to dendritic cells and B lymphocytes. Antibodies to gp 160 or gp 120 sometimes lead to concentrations of virus in the lymph nodes and spleen. The '543 approach, like the others, would preserve transmembrane protein gp41 and some or all of the viral membrane.

At any rate, this preserved viral structure can hold unintended consequences. First, as described above gp160, gp120, and gp41 provide binding sites for complement factor H. (Pinter, Claudia et al, Aids Research and Human Retroviruses, Vol. 11 (5), pp. 577-88 (1995)(Pinter, Claudia, et al., Aids Research and Human Retroviruses, Vol. 11(8) (1995)) (Stoiber, Heribert, et al., Immunobiology, Vol. 193, pp 98-113 (1995)) Accordingly, the retention of these structures means that factor H will interfere with humoral immune response following vaccination. The removal of gp120 gp160 in U.S. Pat. No. 6,107,543 may mitigate this effect to some degree; nevertheless, the preservation of the gp41 Factor H binding sites would work against the immunogenicity of the composition. Second, both approaches are silent as to the cellular plasma membrane and retain some or all of the viral membrane, including certain bound proteins that interfere with immune response. As an assembling, replicating HIV particle buds through the infected cell plasma membrane, the membrane is enriched by CD55 (the decay accelerating factor) and CD59 (the homologous restriction factor) that regulate complement. These molecules are incorporated into the viral membrane upon budding from infected cells. Preservation of some or all of these features or structures could interfere with complement activation and humoral response. (Saifuddin, 1995) Third, HIV surface components bear sialic acid, which could remain on the preserved structure of inactivated HIV. Sialic acids are typically found on host proteins and cellular structures; high sialic acid content on a virus, even if the virus were inactivated, would limit the host's ability to recognize the virus and respond properly. Importantly, sialic acid residues are also used in the binding of factor H. (Meri, Seppo, et al., "Discrimination Between Activator and Nonactivators of the Alternative Pathway of complement Regulation: Regulation Via a Sialic acid/Polyanion binding site on Factor H." Proc. Natl. Acad. Sci., USA, Vol. 87(10), pp. 3982-6 (May 1990)) (Blackmore, T. K., et al., J. of Immunology, Vol. 157(12), pp. 5422-7 (December 1997)) (Kuhn, S., et al., Eur. J. Immunol., Vol. 26(10), pp. 2383-7 (October 1996)) (Pangburn, M. K., et al., J. of Immunology, Vol. 164(9) (May 2000))

The present invention is directed to an immunogenic composition that addresses these issues. It is intended that by creating compounds available to target different subtypes and aspects of HIV, it will advance treatment and research. Ultimately, it is hoped to extend survival and to improve the quality of life for infected individuals.

SUMMARY OF THE INVENTION

HIV is among the viruses sensitive to inactivation by psoralen. The viral structure is preserved during the process of psoralen inactivation. This preservation is advantageous for the production of broad based antigenic response. In the present invention, the inactivated viral structure is modified to remove or neutralize selected features that would interfere with immune response. In particular, sialic acid and certain binding sites for complement factor H are neutralized; in some cases the outer cellular plasma membrane may be removed. The primary effect of this treatment is to obviate interference with immune humoral response by human complement factor H and other regulators of complement activity (RCA). In addition, the removal of sialic acid reveals to the immune system that viral components are distinct from the host.

The present invention is tailored to the genotype of virus presented. HIV replicates rapidly and mutates readily through reverse transcriptase and recombination. Each group, subtype, sub-subtype, and circulating recombinant form of HIV-1 and HIV-2 is structurally unique. Missing a subtype could pose serious consequences. For an immunogenic composition to be effective, it must take into account not only interference by preserved structure, but each viral group, subtype, sub-subtype, etc. of concern under the given circumstances. Thus, a vaccine may be tailored to the viral strain(s) present in the host. Accordingly, the composition may preferably be generated from a genetically relevant sample; in the case of a composition intended for the vaccine of an infected host, for example, the relevant sample may be drawn from or matched to the host person. In the case of a composition intended for the vaccine of an uninfected human or other animal, then the relevant sample may be based on a probabilistic assessment of the risk of exposure for that human or other animal.

Accordingly, the present invention is a composition capable of invoking an immune response, wherein certain predetermined strains of HIV relevant to the use of the composition are isolated and inactivated using psoralen and exposure to ultraviolet light. The present invention is further characterized by the removal of certain features from the inactivated HIV that impair immune response. The composition may further comprise pharmacological carriers, stabilizers, or excipients.

DESCRIPTION OF THE INVENTION

Figure 1:
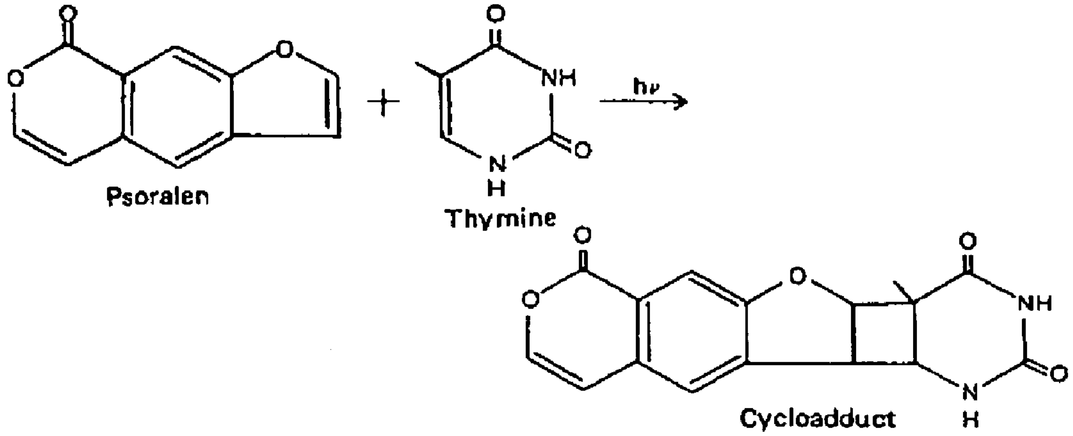
FIG. 1 shows Psoralen formation of photoadducts with nucleic acid upon exposure to ultraviolet light.

As noted above, the general use of psoralen for inactivating HIV to produce an immunogenic composition or vaccine is known. However, the mutability of HIV and its ability to interfere with immune response can impair the performance of prior undertakings. The present invention is an immunogenic composition and method directed to the problems posed by preserved features of viral structure, the high rate of HIV mutation, and HIV resistance to immune response. The present invention is immunotherapeutic, in that it involves the use or stimulation of the immune system with respect to a specific condition or sensitivity. The immune system of concern may be that of a human or any other animal, such as a chimpanzee or mouse. As used here, immunotherapy encompasses the tailoring of an immunogenic composition to optimize performance in the context of the highly mutable genotype combined with active viral interference with immune response. It is intended that the present invention advance diagnostic procedures, analyses, and evoke an immune response in animals. It is also contemplated that given the development of an effective immunogenic composition, a vaccine may be developed and administered using the composition in order to produce immunoprotective factors within a patient.

Accordingly, one aspect of the present invention is a composition capable of invoking an immune response, wherein certain predetermined strains of HIV relevant to the use of the composition are isolated and inactivated using psoralen and exposure to light, and further where features of HIV that impair immune response are removed from the inactivated HIV. The composition may further comprise a pharmacologically appropriate carrier, stabilizer, or excipient.

In an alternate embodiment intended for use as a vaccine for an infected animal, the vaccine may include those strains present in the animal at the time the sample was drawn, matching the genotype of the vaccine to that of the infection. Alternatively, a preventive vaccine may include strains of concern based on probability of exposure. The vaccine may be treated to remove features of the HIV that impair immune response.

Another aspect of the invention is a method of preparing an immunogenic composition comprising determining the strains of HIV relevant to the use of the composition, inactivating the strains using psoralen and exposure to light, and removing or modifying features of the HIV that impair immune response. In particular, these features or components may comprise the complement Factor H binding sites for gp160, gp120, and gp41, removal of sialic acid residues, and optionally the outer cellular plasma membrane. Therefore, a methodology of the present invention comprises for preparation of an immunogenic composition includes:

1. Determining the strains of HIV that are of concern
2. Isolating and culturing the strains of concern
3. Separating the virus from the culture media
4. Optionally removing the cellular outer plasma membrane
5. Adding psoralen and a DNA-repair enzyme blocking agent
6. Irradiating with ultraviolet light
7. Removing or neutralizing CD55 and CD59
8. Desialation of the inactivated virus The present invention is thus an immunogenic composition comprised of a tailored combination of psoralen inactivated HIV subtypes, and a method of preparing and using the same.

Determination of Relevant Strains

The determination of the strains of HIV will depend on the embodiment and application of the present invention. There are a wide variety of applications for immunogenic compositions; accordingly, the following should be construed as exemplary and not limiting. The determination of HIV strains that are relevant may be considered in three exemplary categories: (i) research related, development, analytical; (ii) therapeutic; and (iii) preventive.

In one category of embodiments, the immunogenic composition may be contemplated for use in research or clinical analysis. For research, the strains of concern will be determined by the objectives of the scientific investigation. That is, the procurement, isolation, and culture of the HIV virus will accord with the investigatory design and objectives. The determination of relevant strains for medical research may likely parallel that for any envisaged therapeutic or preventive need, such as vaccine development. Purely academic research may encompass aspects such as the development of research tools or expanding knowledge about strains unrelated to the HIV epidemic. The immunogenic composition may also be useful in studies of immune response, viral evolution, epidemiology, and analysis of viral behavior.

In another category of embodiments, the immunogenic composition may be intended for administration to an HV infected human (or other animal or host), possibly as a therapeutic vaccine. In general, multivalent immunogenic compositions should have the ability to induce an immune response against diverse viral isolates; in the past, this multivalence would involve a combination of inactivated viral particles from a variety of strains of concern. However, HIV within an individual host is rarely static, and continues to evolve through genetic mutation and recombination. Past efforts to target common strains or variants in a multivalent HIV vaccine rely on macroscopic public health predictors and conservative over sampling of HIV strains. In the present invention, the strains of HIV may be genotyped and isolated from a sample drawn from the infected human or other animal. That is, peripheral blood mononuclear cells (PBMC) or other sample may be drawn in order to identify the HIV present in the infected human or other animal. Any typing method appropriate to the circumstances may be used, including sequence based diagnostic genotyping, heteroduplex mobility assay (HMA), analyte specific reagents assay genotyping, molecular diagnostics, gene detection products, and DNA probe-based products. A vaccine may then be composed of those strains present in the human at the time the sample was drawn. Thus, in one embodiment, the HIV in a human (or animal model) is genotyped and the information is used to create a composite vaccine composed of stock components derived from inactivated virus for each of the identified strains. As described below, this alternative may involve a vaccine derived from virus cultured from human PBMCs in vitro or other sample drawn from a person (or other animal) that then undergoes the process of psoralen inactivaton before being re-introduced into that person or other animal as an immunogen. In this way, the immunotherapy is tailored to the genotype of that host's virus. The methodology of the present invention contemplates a plurality of samples to identify and address changes in strain dominance or composition over time and, in response, enable changes in treatment. When a dominant strain is destroyed, a distinct but related resistant variant may then emerge, requiring further immunotherapy.

In another category of embodiments, the immunogenic composition may be contemplated for administration to an uninfected human, possibly as a preventive vaccine. In the past, the preventive composition and administration have been similar to that used in therapeutic multivalent compositions; such compositions may be based on the combined use of viral particles from a wide variety of strains intended to induce a broad immune response. Such an approach is contemplated as one embodiment of the present invention in preventive form.

Alternatively, the present invention in a preventive embodiment may also be based on a probabilistic assessment of the risk of exposure for that person. Notably, U.S. Pat. No. 6,503,753 contemplated personal preventive vaccines in cases where the risk of transmission was primarily through a particular individual; accordingly, the inactivated strains may be derived from a sample drawn from that infected individual. Such personal vaccines could be used as an embodiment of the present invention. Likewise, laboratory workers or healthcare professionals may face heightened risk from occupational exposure to certain known strains and may benefit from improved immune response to those specific strains. Alternatively, strain determination for personal vaccines may be based on behavioral and demographic risk factors for HIV infection in geographic areas of concern. Such analysis could consider behavioral patterns in the context of historic, epidemic, and geographic data supporting an exposure probability analysis. In geographic areas where the epidemic has spread beyond groups with identifiable risk factors, then multivalent prevention could reflect all known strains by geographic area of concern.

Procurement and Preparation for Irradiation

The following embodiments are to be considered exemplary and not limiting, as there are well established methods for procurement, isolation and culturing viruses. In fact, the actual virus may be procured in a variety of ways. Individuals infected with the HIV strains may be sampled and the virus may be isolated, purified, cultured, and typed using procedures that are known in the art, and are in part discussed below. Such samples may be drawn from PBMC or other fluids, such as saliva, or tissues, such as relevant mucous membranes; however, as is known in the art, PBMC may be preferable for its inclusion of immune components, depending on the application. Alternatively, HIV may be procured from existing samples of known commercial viral stocks or laboratory isolates. Viral particles may also be produced by transformation of cells with viral-encoding vectors, which is the uptake of foreign genetic material into a cell. Transformation is usually accomplished by physical means such as co-precipitation of the DNA with insoluble calcium chloride. (Nicholls, Desmond, An Introduction of Genetic Engineering (2nd ed. February 2002)) Transformed DNA can either exist in the cell as an episomal (extra chromosomal) element or be integrated within the nuclear genome. The efficiency of a DNA transfer into cells depends on the particular method used. The descriptions below may be common to the various categories of embodiments herein, unless otherwise specified.

The present invention contemplates various preferable culture media. A first preferable culture media is the PBMC drawn from an HIV infected host. In this embodiment, the HIV cells would replicate within the preserved in vitro host environment. Such a media may be safer and simpler for subsequent administration to the host. However, many culture media such as human cells or yeast include DNA-repair enzymes that can reverse the effect of psoralen. These enzymes can repair DNA and RNA through transcription coupled repair and global genomic repair. Thus, culturing in PBMC or yeast cells would be improved by inhibition of any enzymes that would tend to repair the DNA and RNA following exposure to psoralen and ultraviolet light. In a preferred embodiment, such media may be treated with repair enzyme inhibitors such as novobiocin, aphidicolin, or both. (Brenneisen, Peter, et. al., J. of Biological Chemistry, Vol. 275(6), pp. 4336-44 (Feb. 11, 2000)) (Niggli, H. J., Mutation Research, Vol. 295(3), pp. 125-33 (August 1993)) (Cleaver, J. E., J. of Cancer Research, Vol. 47(9), pp. 2393-6 (May 1987)) (Rosentein, B. S., et al., Environmental Mutagenis, Vol. 8(3), pp. 335-43 (1986)) In another preferred embodiment, the culture media is any media lacking or having low levels of such DNA-repair enzymes, such as Fanconi anemia type C. Fanconi anemia type C has a deficiency of DNA-repair enzymes, reducing recombination and making it preferable for use with psoralen inactivation. Some mutant cultures are known to be defective in excision repair of UV-induced pyrimidime dimers and are hypersensitive to photo addition of both mono and bi-functional psoralens. Examples are uvrA, B, or C mutants of *escherichia coli*, of RAD3 type units of *saccharomyces cerivisiae*, Chinese hamster ovary cancer cells complementation groups 1 and 4, Xeroderma pigmentosum groups A and D. Other culture media may be functionally equivalent so long as the operation of UV light damage DNA-repair enzymes is inhibited.

For an HIV negative human (or animal) a suitable vaccine/immunogen can be produced by culturing the virus in vitro before psoralen inactivation. Many culture media are available but a preferred embodiment would be a human's own peripheral blood mononuclear cells (PBMCs). This would subject the virus to a selective pressure generated by the human's own immune system. The strain(s) of HIV that replicate in vitro in such a culture would be the strains the human would most likely replicate in vivo in producing an active infection. Therefore each HIV negative and HIV positive human could have a tailored made vaccine.

Separation of the virus from culture cells may be accomplished by centrifuging the cells for ten minutes at 2000 rpm and at 4° C. The supernatants may then be filtered twice through a 0.22 millimicron Millipore filter.

In some cases, it may be desirable to remove host cellular outer membrane or membrane particles that could impede access to the viral components. In that case, disruption or removal of the outer membrane can be accomplished by means that are known in the art, such as treatment with ethanol, detergents, phenols, or other solvents. Importantly, removal of the outer membrane should not otherwise alter the viral structure or denature any viral proteins. (Levinson, Warren, Medical Microbiology & Immunology: Examination and Board Review (7th ed. July 2002)) In a first embodiment, such removal may be accomplished by detergents; detergents are "surface-active" agents composed of a long-chain lipid soluble hydrophobic portion and a polar hydrophilic group. The hydrophilic group may be a cation, an amine, a non-ionic group or multivalent. Surfactants interact with the lipid in the cell outer membrane through their hydrophobic chain and with the surrounding water through their polar group and thereby disorganizes the outer membrane. Quaternary ammonium compounds, such as benzalkonium chloride are cation detergents widely used for skin antisepsis and would be preferable for application here. Alternatively, ethanol will disorganize the lipid structure in the outer membrane; uncontrolled, it could denature proteins—which may be a limiting factor. Ethanol is more effective when diluted with water, for example, 70 percent ethanol is preferable to 100 percent. Thirdly, phenols such as hexachlorophene or cresol may be appropriate in some embodiments. The use of any of these substances should be under conditions that preserve the antigenic nature of the inactivated virus, preserves the viral structure, and avoids denaturing of the viral proteins.

The inactivation agent is preferably psoralen, as it is able to preserve the antigenic properties of the viral structure while inactivating RNA and DNA. Psoralens are a class of photomutagenic and photo-chemotherapeutic compounds that covalently modify nucleic acids. They belong to a family of small molecules that intercalate and photoalkylate DNA and RNA (both single stranded and double stranded.) The primary targets of psoralens are thymidine residues in DNA and uracil residues in RNA; these molecules form both monoadducts and interstrand cross links. The reaction takes place between the 3,4 (pyrone) or 4',5' (furan) double bonds of the psoralen and the 5,6 double bond in pyrimidines. The photobinding of psoralens to double strand DNA (dsDNA) results in substantial structural distortion of the normal DNA double helix. (Spikes, John D., Photosensitization in Mammalian Cells, Ch. 2 (1983)) (Averbeck, D., et al., Mutagenic Effects of Psoralen-Induced Photo adducts and Their Repair in Eukaryotic Cells, Pp. 933-59 (1988))

The immunogenic composition for one or more predetermined subtypes of HIV may be prepared for irradiation as follows. The HIV virions of concern in culture may be diluted in a solution containing 4'-aminomethyl 4,5', 8-trimethylpsoralen (AMT). Psoralen derivatives readily pass through cell walls and through virus coats and can then photoreact after exposure to UV light with the nucleic acids inside, producing pyrimidine dimers. AMT cross-links the viral RNA and DNA. All psoralens are photoactive.

Irradiation

Upon exposure to UV light, the psoralens form photoadducts with nucleic acids. This process does not require oxygen, and preferably oxygen should be removed. Psoralens can be irradiated before the addition of nucleic acids and photoadducts will still result. The HIV virus can then be inactivated with AMT and UV light. The virus is then unable to replicate its nucleic acid because the cross-linked DNA or RNA cannot be copied. The virus is thereby "killed" by inactivation of its DNA or RNA. Because photoreaction blocks the replication and expression of nucleic acid, it forms the basis of a technique for eliminating the infectivity and virulence of viruses. The surface of the virus remains largely unmodified, rendering the inactivated virus potentially useful for vaccines.

Psoralen photo-inactivation has proved to be superior to conventional inactivation techniques, such as formaldehyde treatment, for the preservation of antigenicity and immunogenicity in experimental inactivated vaccines. (Hanson (1992)) Photoreaction with AMT has been shown to remove the HIV infectivity from HIV-infected cells without altering antigenic surface properties; these inactivated cells retain normal reactivity with monoclonal antibodies to a variety of both cellular and viral antigens. (Hanson, 1992)

In HIV infected cell cultures, numerous DNA transcripts of the viral genome are produced in the infected cell and may eventually spill from lysing cells into the culture medium. While it is not known if such DNA or RNA poses a hazard of transfection or transformation, the psoralen photoreaction would be expected to inactivate this free DNA and if anything even more rapidly than it inactivates the RNA-containing virions, thus providing a safety factor not available from conventional inactivating techniques such as heat, alcohol or detergent. Furthermore heat, alcohol or detergent cannot evenly inactivate the RNA and DNA of viruses. (Hanson, 1992)

The kinetic mathematics of psoralen inactivation is frequently nonlinear and can show a "tailing off" effect. This tailing off probably results from loss of psoralen activity during the virus irradiation due to photodegradation of the psoralen itself. Preferably, periodic addition of psoralen during virus inactivation will maintain linear kinetics. The loss of psoralen activity parallels viral inactivation. Two successive steps of irradiation are preferable for effectiveness and for creating higher safety margins for the vaccine. For example, a first exposure of 405 nm wavelength followed by a 365 nm wavelength exposure is preferable for a higher production of cross links capable of disabling a DNA or RNA molecule. In embodiments where a single exposure is required, then a 365 nm wavelength exposure is preferable. The dose rate shall be appropriate for the psoralen absorption under the circumstances; excess dose rate beyond viral inactivation may lead to photodegradation of viral proteins.

Preferably, a sample of the irradiated viral cells may then be cultured and analyzed to ensure inactivation and to eliminate the possibility of residual infectivity.

Treatment of Structural Features that Could Impair Immune Response

Regulators of complement activity, such as CD55 and CD59 should preferably be removed from the composition. These surface glycoproteins play a role in inhibiting complement. CD55 destabilizes both C3 convertases (C4b,2b and C3b,Bb) and both C5 convertases (C4b,2b,3b and C3b,Bb, C3b). CD59 and other homologous restriction factors are cell-surface expression proteins that inhibit the intercalation of C9 into the plasma membrane, protecting blood cells, vascular endothelial cells, and other tissues from lytic damage by complement cascade. (Hoffman, 1999) CD55 and CD59 are membrane bound and preferably may be selectively removed by treatment with Phosphatidylinositol-specific Phospholipase C(PI-PLC). This will remove all of the glycosylphosphatidylinositol (GPI) linked proteins, including CD55 and CD59. Such selective enzyme cleavage is among known treatment methods.

Desialation of the inactivated composition is a beneficial step. Preferably, the sialic acid residue from HIV may be removed by treatment with neuramimidase enzyme. Neuramimidase cleaves sialic acid. (Hart, Melanie L., et al., AIDS Res Hum Retroviruses, Vol. 18(17), pp. 1311-7 (2002)) (Meri, 1990) Many of the mannose sugar moieties are protected from the immune system by a coating of sialic acid residue. Sialic acid is found on normal human cells and tissues, and is used by the immune system for "host recognition." In doing so, the immunologic response against "host" structures is limited. Sialic acid residues are also found on the heavily glycosylated envelope of HIV. (Hart, 2002) If the sialic acid residues are removed, then Factor H will not bind to HIV and the vaccine would then be identified as "foreign" by the immune system, so that a robust immunologic response will occur. (Hart, 2002) Other neutralization or desialation methods consistent with the present invention may also be used, such as treatment with trypsin.

In general, treatment of the structural features may be conducted at a variety of points in the preparation of the composition. Desialation is preferable after exposure to psoralen and irradiation with ultraviolet light, in that desialation of active HIV can increase viral replication and infectivity. (Hart, 2002)

Preparation for Administration

The present immunogenic composition may be mixed with appropriate immune stimulant or adjuvant, including those described as alternative embodiments below. Such compositions may be used as are appropriate for the application. Customary stimulants or adjuvant known in the art include incomplete Freund's adjuvant, liposomes, etc. A preferred embodiment includes one or more stimulant taken from customary adjuvants and/or those compositions described further herein.

The immunogenic composition may also be mixed with pharmaceutical or laboratory compositions appropriate for the anticipated method of use or administration, such as carriers or excipients, such as mineral oil.

HIV Strains and Subtyping

As noted above, HIV has a diverse genotype. The high level of genomic diversity of HIV complicates diagnosis and treatment of strains that can vary in infectivity, transmissibility, and immunogenicity. The investigation of multivalent immunogenic compositions will necessarily incorporate a plurality of strains. Phylogenetic analysis may be undertaken using resources from HIV sequence databases known to those in the art, and as described herein.

The acquisition, isolation, and identification of HIV subtypes and sub-subtypes are well described in the field. (Robinson, D. L., et al., HIV-1 Nomenclature Proposal: A Reference Guide to HIV-1 Classification (September 1999)) For the present invention, subtyping HIV may be performed using any medically appropriate means known to those skilled in the art. Genotyping is a direct means for identifying HIV-1 subtypes. Serotyping or analysis of subtypes by antibody response of an infected person is an alternate, indirect means. DNA and RNA sequencing or genotyping kits are preferable when they include phylogenetic analysis to detail the subtypes of concern. Subtype probes and assays of env and gag (heteroduplex mobility assays or HMAs) are alternative, but possibly limited techniques. (Salminen, Mika, Nat'l Pub. Health Inst. (1994)) (Buonaguro, Luigi, J. of Virology, Vol. 69, No. 12 pp. 7971-7981 (1995)) In general, higher volume subtyping may be limited to discriminating fewer subtypes.

The individual HIV-1 groups M (major), 0 (outlier) and N (non-major/outlier) may have arisen from separate transmission events; HIV-1 is somewhat similar to chimpanzee SIV. Phylogenetic diversification within each of these groups into subtypes or clades resulted from genetic mutations. Group M strains are primarily responsible for most HIV infections, while groups O and N strains are isolated largely from individuals from Cameroon.

The HIV-1 group M subtypes and sub-subtypes appear to have genetically diverged in humans from a common source. The members of group M are broken out into nine equidistant phylogenetic subtypes. These are labeled A1, A2, B, C, D, F1, F2, G, H, J and K. The sequences within any one-subtype or sub-subtype share more genetically than they do with sequences from other subtypes throughout their genomes. Subtypes constitute different lines of HIV, and may be statistically associated with social or geographic factors. Thus, the subtyping system identifies genetic clusters; it can be used for locating subtype specific biological differences or similarities in HIV components, such as proteins. As an additional complication, viruses within a subtype may evolve at different rates, while subtypes may also vary in rates of evolution.

Retroviruses have a tendency to recombine with related retroviruses. This recombination is another contribution to genetic diversity. The process of recombination creates variants, drug resistance, and modified expression of antigenic characteristics. The circulating recombinant forms (CRF) of HIV are recombinant HIV-1 genomes that have made an epidemiologically relevant effect in the HIV-1 epidemic. CRFs of HIV are characterized by identical mosaic structures. Recombination can occur during reverse transcription, when there is alternate switching of templates between both genomic RNA strands co-packaged in each of the virions. If the two strains belong to different subtypes of the HIV-1 M group, then the result is a mosaic genome composed of regions from each of the two subtypes; that is, the viral reverse transcriptase enzyme switches templates from one of packaged RNA genome to the other during reverse transcription after the co-packaged genomes enter a new cell.

These inter subtype mosaics are commonly found in multiply-infected individual patients. If there is transmission of an inter-subtype recombinant virus, then it can create a circulating strain within the HIV epidemic. CRFs are labeled with numbers in which they were first described. As of 2002, there were nearly 3 million CRF infections; CRF infections are becoming more likely, adding to genomic diversity.

Although genetically and antigenically related, HIV-2 is biologically and epidemically distinct from HIV-1. Different groups of HIV-1 have been located throughout the world, while HIV-2 has been located predominately in Africa, Europe, and India. HIV-2 is related to SIV isolated from the Sooty-mangabey. The sequences from the HIV-2 A, B, C, F or G clades are distinct from those in the D and E clades, leading to the conclusion that each group of HIV-2 represents a separate transmission event. HIV-2 appears to have lower infectivity and pathogenicity.

Description of Additional Embodiments

In an alternative embodiment, the composition may be bound covalently or otherwise to polysaccharides composed of mannose or mannan. Binding or coupling may be accomplished using methods known to those in the field. Mannose is a sugar found only on microorganisms and pathogens not ordinarily found within the human body. Mannose binding protein (MBP) is a colectin, a C-type lectin that contains regions of collagenous structure. It is present in normal human serum and consists of subunits each composed of three polypeptide chains, forming a collagen-like triple helix and three C-terminal globular carbohydrate recognition domains (CRDs). Six subunits together form an overall structure resembling the bouquet of tulip-like structure of C1q of the classical complement pathway. Binding of MBP to carbohydrate initiates the classical complement pathway to the activation of $C1r_2$ $C1s_2$. This may result in complement killing either directly through insertion of the terminal membrane attack complex or through opsonization by deposition of complement on the microbial surface. MBP may also activate C2 and C4 via another newly described serine proteases called MASP (1 and 2) serine proteases. Thus, MBP also exhibits complement independent opsonizing activity, probably mediated by binding of the collagenous stalks to the colectin receptor of phagocytic cells. (Prodinger, W. M., et al., Fundamental Immunology, Ch. 29, pp. 967-95 (4th ed. 1999)) (Speth, Cornelia, et al., The Middle Eu. J. of Medicine, Vol. 111 (10) pp 378-391 (1999)) Any organism with mannose or mannan on its surface will stimulate the lectin pathway of complement activation. A composition bound to such polysaccharides will bind with mannose binding lectin in the serum, activating the lectin pathway of the complement system. Thus, this alternative embodiment would thereby enhance the overall immunologic response to the vaccine.

In another alternate embodiment, the composition may be combined with substances that stimulate or activate the alternative complement pathway. For example, it is known that certain forms of teichoic acid are potent activators of the alternative complement pathway. (Winkelstein, J. A., et al., J. of Immunol., Vol. 120(1), pp. 174-8 (January 1978)) In addition, zymosan, which may be derived from yeast cells, can induce cytokines and stimulate immune response in conjunction with the alternative pathway of the complement system. Zymosan is phagocytosed by macrophages with or without opsonization, and therefore has a useful immunologic property of activating the alternative pathway of complementation. The zymosan macrophage interaction is believed to enhance the Th-1 response. CD4 cells can be divided into Th-1 and Th-2 cells. Th-1 cells activate cytotoxic T cells by producing IL-2; whereas Th-2 cells form the B-cell helper function by producing primarily IL4 and IL-5. The level of Th-1 response produced by zymosan is regulated by C3 cleavage fragments, C3b and iC3b. The amplified C3b deposits on the acceptor surface of zymosan and assembles macrophages, dendritic cells, or other antigen-presenting cells. Macrophages, dendritic cells, or other antigen-presenting cells make an antigen presentation to Th-1 cells after opsonizing zymosan, and after antigen-specific macrophage activation occurs. (Ara, Yuki, et al., Immun. Vol. 103(1), pp. 98-105 (May 2001)) Zymosan can therefore be used as an immune stimulant; it enhances both humoral and cell-mediated immune responses to HIV disease. Thus, the composition may be bound covalently or otherwise to substances that stimulate the alternative complement pathway, such as teichoic acid or zymosan.

Figure 2:
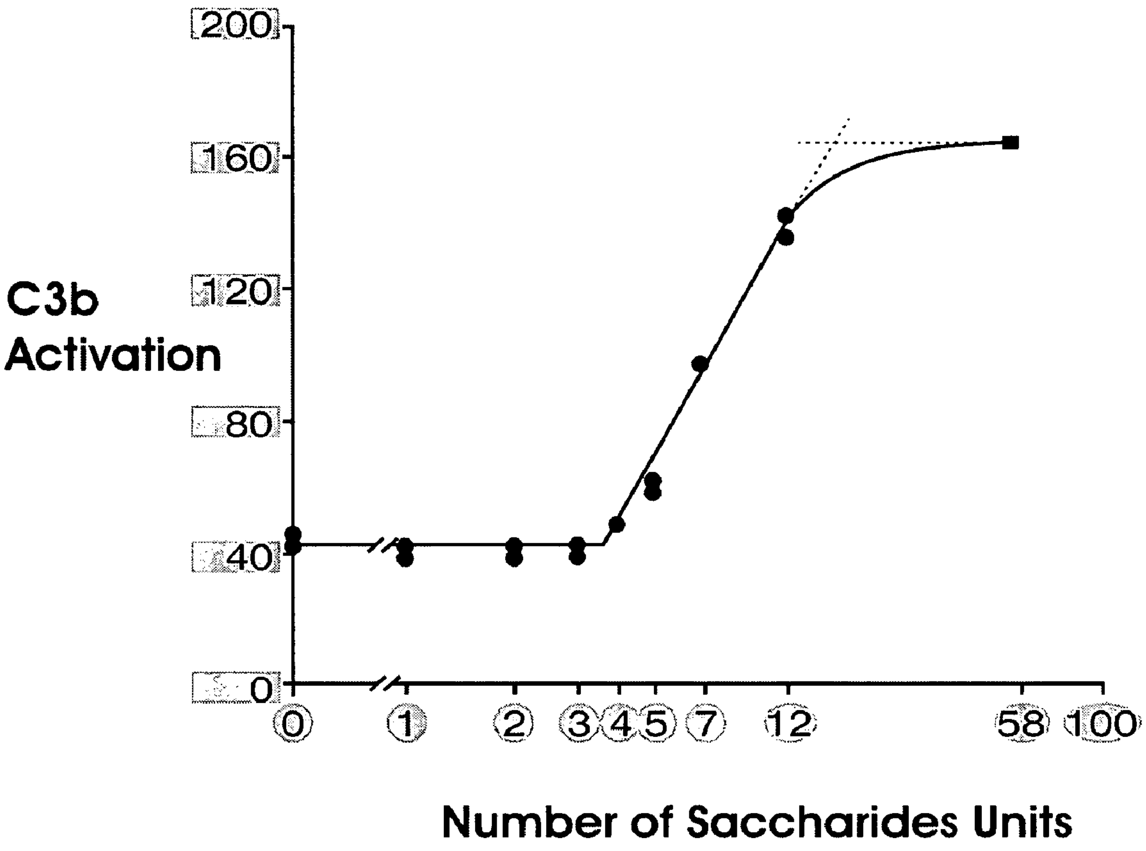
FIG. 2 demonstrates how increasing polysaccharide length enhances immunogenicity up to a maximum of 16 monosaccharides.

Therefore, to enhance immunogenicity, mannose, teichoic acid, zymosan, or some combination thereof may be bonded to protein components of the composition. Preferably, the polysaccharides may consist of sixteen separate saccharide units. (Pangburn, M. K., 1989) The preferred source for the carbohydrate/stimulant component of the composition would be the capsular polysaccharide of the yeast cell, Cryptococcus neoformans serotype C. (Sahu, Arvind, et al., Biochem. J. Vol. 302, Part 2, pp.429-36 (Sep. 1, 1994)) This yeast cell exhibits four branching xylose sugars from each trimannose repeat unit. FIG. 2 demonstrates the loss of activity of Factors H and Factor 1 on C3b with increasing polysaccharide length to a maximum of 16. If such yeast is likely to introduce DNA repair enzymes, then the enzymes are preferably to be inactivated using the methods described above.

Additionally glucose molecules and polysaccharides may be removed from the composition. Glucose inhibits both the rate and the extent of C3b deposition. (Sahu, 1994) Glucose may be removed by adding insulin to cell cultures.

In an alternate embodiment, the effect of heparin may be inhibited. Heparin is a cofactor necessary for effective Factor H function. (Linhardt, Robert J., et al., Biology Chemistry, Vol. 263(26), pp. 13090-6 (Sep. 18, 1988))(Maillet, Francoise, et al., Mol. Immun., Vol. 25(9), pp. 917-23 (1998)) (Blackmore, 1996)(Blackmore, 1998) (Giannakis, Eleni, Immunopharmacology, Vol. 1(3), pp. 433-43 (October 2001)) Factor H is a major limiting protein in the alternative complement pathway. The alternative complement pathway is the first arm of the immune system to respond to microorganisms or vaccines. Protamine binds heparin and is used to reduce the effective heparin in patients undergoing anticoagulation. (Maillet, Francoise, et al., Molecular Immun., Vol. 20(12), pp. 1401-4 (December 1983)) (Weiler, John, et al., J. Exp. Med., Vol. 147(2), pp. 409-21 (February 1978)) Recently, a less toxic heparin antagonist, low molecular weight protamine (LMWP) has become available. Protamine, or preferably LMWP for this embodiment, may be included as a component in order to impair the activity of Factor H in limiting the alternative complement pathway. (Liang, J. F., et al., Biochemistry, Vol. 68(1), pp. 116-20 (2003)) Alternatively, Heparinase is known to degrade Heparin enzymatically.

In another embodiment sulfated polyanions may be included in the vaccine. Sulfated polyanions absorb Factor H, effectively removing it from circulation. Other polyanions such as dextran sulfate and DNA are activators of Factor H. These polyanions should be removed from the vaccine. Branched partially hydrolyzed polysaccharides of glucose known as dextrans have been used for effective plasma expanders. (Hoffman, 1999) Dextran sulfate is a sodium salt of sulfuric acid esters of the polysaccharide dextran.

Soluble dextran sulfate with a molecular weight greater than 5.times.10.sup.3 is an inducer of the alternative pathway of complement. The number of sulfate groups per hundred glucose residues in the dextran determined the activation potency of the dextran in the alternative pathway. The optimal degree of sulphation was 50-60 $SO_4$/100 glucose molecules. (Burger, R., et al., Immunology, Vol. 29(3), pp. 549-54 (1975))

Sulphated sephadex (SS) is a cross-linked insoluble form of dextran. Like soluble dextran sulphate SS activate the alternative pathway of complement and the classical pathway as well. Three variables control the activity of SS with both pathways of complement activity. (1) Amount of sulphation; the higher the sulphated content up to 15.6% by weight resulted in a higher complement activation. No complement activation was noted with a sulphate content less than 2.43%. (2) Concentration of SS; higher concentrations result in complement activation with a maximum C3 turnover at 40-50 μg/ml. (3) Temperature; maximum C3 turnover was noted at 37.degree. C. with a total loss of activity at 4° C. (Burger, R., et al., Immunology, Vol. 33(6), pp. 827-37 (December 1977))

Both soluble and insoluble forms of dextran (>5000 molecular weight) activate the alternative pathway of complement. This is accomplished by blocking the effect of factor H. (Bitter-Suermann, D, et al., European J. of Immun., Vol. 11 (4), pp. 291-5 (April 1981))

Low molecular weight dextran sulfate (<5000) enhances factor H binding therefore it limits the activity of the alternative pathway of complement. (Meri, 1990) DNA like heparin also increase factor H binding. (Gardner, William D., Biochemical and Biophysical Research Communications, Vol. 94, pp 61-67 (1980))

Therefore to enhance immunogenicity dextran sulfate with a molecular weight>5000 with 50-60 $SO_4$/100 glucose molecules could be included in the compound. Likewise SS with 15.6% $SO_4$ by weight at a concentration of 40-50 μg/ml at a temperature of 37.degree. would enhance the immunogenicity of the compound. Low molecular weight dextran would not be included in the formulation since it would increase factor H binding and decrease complement activation. Finally, DNA enhances complement activity and therefore this immunogen could be used concurrently with a DNA vaccine. (The DPT vaccine is composed of three separate vaccine particles. The pertussis component acts as an adjuvant for the other two. (Parham, Peter, The Immune System, Ch. 12 (2nd ed. 2004)) An analogous situation exists here, where a DNA vaccine for HIV disease would act as a adjuvant for the psoralen vaccine.)

In a further alternate embodiment, substances that stabilize C3 convertase may be used with the present invention. All three complement pathways lead to the production of C3b, which bonds covalently to the surface of microorganisms or components of the microorganisms presented in such an immunogenic composition. C3b is produced by enzymes known as C3 convertase. Cobra venom factor (CVF), derived from the snake Naja kaouthia, stabilizes this enzyme. (Alper, C. A. and D. Balavitch, Science, Vol. 191(4233), pp. 1275-6 (March 1976)) The half life of CVF C3b,Bb C3/C5 convertase is seven hours, in contrast to that of endogenously produced alternative complement pathway C3 convertase (C3b, Bb), which is 1.5 minutes. C3b,Bb is disassembled by Factor H and C3b is inactivated by the combined action of Factor H and Factor I. In contrast Factor CVF,C3,Bb is resistant to all regulatory complement proteins. (Kock, Michael A., et al., J. of Biol. Chemistry, Vol. 279(29), pp. 30836-43 (July 2004)) C3b,Bb requires additional C3b to act on C5 whereas CVF,Bb can cleave C5 directly. Therefore, the CVF,Bb enzyme continuously activates C3 and C5. (Kock, 2004)

The biological function of CVF in cobra venom is believed to facilitate the entry of the toxic venom components into the bloodstream. This is achieved by complement activation causing release of the anaphylatoxins C3a, C5a and Bb, which increase the vascular permeability. (Vogel, Carl, Immunoconjugates, Ch. 9 (1987)) CVF, despite its derivation from cobra venom, is a non-toxic protein; CVF can be isolated from the other enzymes, polypeptides, etc., from cobra venom, which includes toxins.

Figure 3:
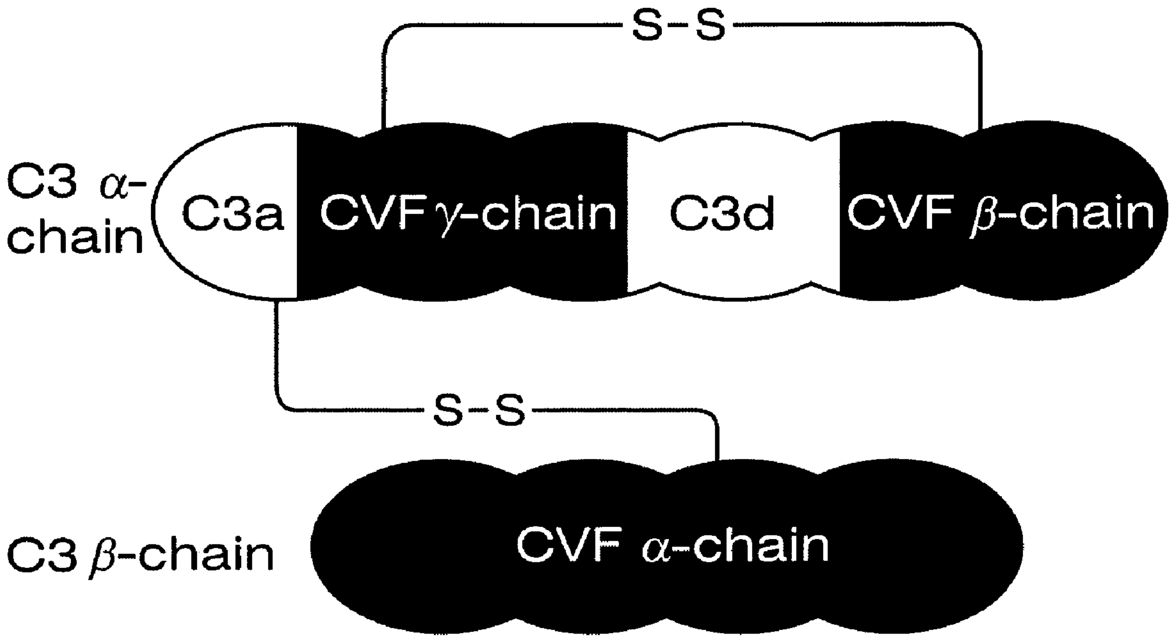
FIG. 3 is a schematic drawing showing the chain structures of C3 and CVF and their relationship.

Thus, administration of CVF results in an explosive production of C3b. (Vogel, 1987) (Kock, 2004) FIG. 3 illustrates the structural homology between C3 and CVF. C3b on the surface of microorganisms is recognized by follicular dendritic cells within the lymph nodes as well as T cells and B cells in the peripheral circulation and within the germinal centers of the lymph nodes. C3b is a powerful opsonin. Opsonins trigger several arms of the immune system simultaneously. (Hoffman, 1999) Thus, in an alternatively embodiment, CVF may be used as a component of the composition.

The preferred form of CVF is dCVF (De-α-galactosylated CVF). (Gowda, D. C., et al., J. of Immunology, Vol. 152(6), pp. 2977-86 (March 1994)) Naturally occurring CVF is characterized by an unusual polysaccharide which is a fucosylated biantennary complex-type N-linked chain containing an α-galactosylated Lex antigenic epitope, Galα1-3Galβ1-4 (Fucα1-3) GlcNAcβ1. Removal of this polysaccharide can be accomplished by incubating CVF with peptide-N-glycosidase F (N-glycanase) at 37° C. for 18 to 23 hours at a ph of 8.0. Removal of this novel polysaccharide from CVF is necessary since 1% of human IgG reacts with the terminal Galα1-3Galβ1 sequence of CVF. However removal of this polysaccharide does not interfere with the complement fixation character of the molecule nor does it result in a shorter half life of the molecule. dCVF will be covalently bound to the polysaccharide unit(s) comprising the immunogenic composition.

In another embodiment, nickel compounds may be added to the composition. It has been shown that nickel is effective in enhancing the C3 convertase activity of both the lectin and the alternative complement pathways. (Fishelson, Z., et al., J. of Immun., Vol. 129(6), pp. 2603-7 (December 1982)) Natural nickel intake for average adults is estimated to be 60 to 260 micrograms per day, with an environmental health reference dose of 0.02 milligram per kilogram body weight per day (mg/kg/d). (U.S. EPA, 2003). It is contemplated that the present invention would include Nickel, preferably nickel chloride, on the order of average daily intake well below the reference dose. Therefore, the present invention may be produced using nickel to enhance immune response.

SUMMARY

In conclusion, the present invention is an immunogenic composition and a whole particle vaccine based on psoralen inactivation of predetermined strains of HIV, wherein certain features that interfere with immune response have been treated. Individual or component vaccines may be created for HIV subtypes or circulating recombinant forms of concern, as listed above or as may be identified in the future.

The process for determining what strain of HIV should be included in the immunogenic composition depends on the contemplated application. For a therapeutic example, a PBMC specimen may be drawn from an HIV positive patient; and from this sample appropriate regions (e.g., env gp41, gag p24) of the HIV genome may be isolated, amplified and sequenced to determine the HIV subtype. Phylogenetic analysis may be undertaken using resources from HIV sequence databases. At the same time, viral loading may be assessed.

A methodology of the present invention comprises for preparation of an immunogenic composition includes:

1. Determining and isolating the strains of HIV that are of concern
2. Culturing the strains, optionally in a DNA repair enzyme deficient culture
3. Separating the virus from the culture media
4. Optionally removing the cellular outer plasma membrane
5. Adding psoralen and optionally a DNA-repair enzyme blocking agent
6. Irradiating with ultraviolet light
7. Removing or neutralizing CD55 and CD59
8. Desialation of the inactivated virus
9. Optionally adding appropriate immune stimulants or adjuvants To prepare the composition that constitutes the composite vaccine agent for the invention, it is possible to use known methods of purification, synthesis, or genetic engineering for each of the components. Practitioners skilled in the art may isolate and inactivate viral strains in the preparation of the vaccines. These may be incorporated into pharmaceutical compositions appropriate for the anticipated method of administration, such as carriers or excipients. A patient requiring treatment may be administered the present invention in amounts sufficient to ameliorate immune response;

that is, a therapeutically effective dose would be that amount necessary to reverse specific immune suppression in an HIV positive patient to the extent desired, and determined using standard means, such as Chromium Release Assay, Intracellular Cytokine Assay, Lympho-proliferative Assay (LPA), Interfero'n Gamma (IFN-gamma) ELISpot Assays, and preferably MHC Tetramer Binding Assays. These same laboratory tests would be applied to measure the immune response of an HIV negative patient. The therapeutically efficacious or effective dosing and dosing schedule would depend on the patient's age, gender, and co-morbid diseases. Furthermore, the potential for pregnancy is a factor in treatment of women of child bearing potential.

The analysis and development of the immunogenic composition should incorporate a wide range of doses of inactivated particulate for evaluation. Animal trials should consider differences in size, species, and immunological characteristics; it is anticipated that immunological differences between humans and animals may relegate animal trials to toxicity analysis. Clinical trials will involve at least the standard three phase model, ranging from safety and dosage in a small population, safety and immunogenicity in a second phase of several hundred volunteers, to a large scale effectiveness phase. A starting dose for trials may be 10 micrograms/strain for juveniles and 20 micrograms/strain for adults. Testing should contemplate particulate concentration in the wide range of $10\text{-}10^{20}$. The clinical trials should include appropriate exclusionary criteria as is customary, such as exclusion for other immune suppression conditions, pregnancy, active drug use, etc.

Administration may be made in a variety of routes, for example orally, transbucally, transmucosally, sublingually, nasally, rectally, vaginally, intraocularly, intramuscularly, intralymphatically, intravenously, subcutaneously, transdermally, intradermally, intra tumor, topically, transpulmonarily, by inhalation, by injection, or by implantation. etc. Various forms of the composition may include, without limitation, capsule, gelcap, tablet, enteric capsule, encapsulated particle, powder, suppository, injection, ointment, cream, implant, patch, liquid, inhalant, or spray, systemic, topical, or other oral media, solutions, suspensions, infusion, etc. In addition, the present invention may be combined with other therapeutic agents, such as cytokines, including natural, recombinant and mutated forms, fragments, fusion proteins, and other analogues and derivatives of the cytokines, mixtures, other biologically active agents and formulation additives, etc. Those skilled in the art will recognize that for injection, formulation in aqueous solutions, such as Ringer's solution or a saline buffer may be appropriate. Liposomes, emulsions, and solvents are other examples of delivery vehicles. Oral administration would require carriers suitable for capsules, tablets, liquids, pills, etc, such as sucrose, cellulose, etc. Because some of the first targets for infection with HIV are epithelial cells and Langerhans cells in the skin and rectal and vaginal mucosa, then a preferable embodiment of delivery is dermal combined with rectal and/or vaginal suppository. HIV is contracted predominantly by rectal and vaginal intercourse. Therefore rectal and/or vaginal suppository administration of the vaccine would be the preferred administration methodology. The present invention may also be administered in a prime-boost protocol.

While the description above refers to particular embodiments of the present invention, it will be understood that many modifications may be made without departing from the spirit thereof. The accompanying claims are intended to cover such modifications as would fall within the true scope and spirit of the present invention.

What is claimed is:

1. A method for preparing a composition, comprising:

1. culturing, amplifying and purifying an HIV isolate;
2. inactivating the purified virus of step 1 with ultraviolet radiation and psoralen;
3. removing CD55 and CD59 from the inactivated virus of step 2; and,
4. removing sialic acid residues present on the virion membrane.

2. The method of claim 1, wherein said isolate is a primary isolate and said isolate is characterized by genotype.

3. The method of claim 1, comprising an additional step of 5, inhibiting DNA repair enzymes within the composition.

4. The method of claim 1, wherein said culturing is within a DNA repair enzyme deficient culture.

5. The method of claim 1, wherein said culturing is in human PBMC isolated from blood drawn from an infected person.

6. The method of claim 1, wherein CD55 and CD59 are removed by treatment with phosphatidylinositol-specific phospholipase.

7. The method of claim 1, wherein sialic acid is removed by treatment with neuraminidase, trypsin, or other appropriate desialation enzymes.

8. The method of claim 1, wherein CD55 and CD59 are removed by treatment with phosphatidylinositol-specific phospholipase and wherein sialic acid is removed by treatment with neuraminidase.

9. The method of claim 1, further comprising an additional step of 5, removing polyanions capable of potentiating Factor H from the composition.

10. The method of claim 1, further comprising an additional step of 5, adding sulfated polyanions capable of absorbing Factor H.

11. The method of claim 1, comprising an additional step of 5, adding an immune stimulant to the composition.

12. The method of claim 11, wherein the immune stimulant comprises polysaccharides composed of at least one mannose in a form capable of binding to the composition.

13. The method of claim 11, wherein the immune stimulant comprises teichoic acid in a form capable of binding to the composition.

14. The method of claim 11, wherein the immune stimulant comprises zymosan in a form capable of binding to the composition.

15. The method of claim 11, wherein the immune stimulant comprises cryptococcus neoformans serotype C having a polysaccharide capsule capable of binding to the composition.

16. The method of claim 11, wherein the immune stimulant comprises protamine in a form capable of binding to heparin.

17. The method of claim 11, wherein the immune stimulant comprises a heparinase.

18. The method of claim 11, wherein the immune stimulant comprises cobra venom factor in a form adapted to enhance production of C3b.

19. The method of claim 18, wherein the cobra venom factor is dCVF.

20. The method of claim 11, wherein the immune stimulant comprises Nickel in a form adapted to enhance C3 convertase activity.

* * * * *